United States Patent [19]
Kyricos et al.

[11] Patent Number: 5,503,637
[45] Date of Patent: Apr. 2, 1996

[54] APPARATUS FOR PRODUCING AND DELIVERING HIGH-INTENSITY LIGHT TO A SUBJECT

[75] Inventors: Christopher J. Kyricos, Cohasset; Charles A. Czeisler; Richard E. Kronauer, both of Cambridge, all of Mass.

[73] Assignees: Light Sciences, Inc., Brookline; Brigham and Women's Hospital, Boston, both of Mass.

[21] Appl. No.: 967,613

[22] Filed: Oct. 28, 1992

Related U.S. Application Data

[63] Continuation-in-part of Ser. No. 882,172, May 8, 1992, abandoned, which is a continuation-in-part of Ser. No. 819,403, Jan. 10, 1992, Pat. No. 5,304,212, which is a continuation of Ser. No. 365,949, Jun. 15, 1989, Pat. No. 5,176,133, and Ser. No. 521,041, May 9, 1990, Pat. No. 5,167,228, which is a continuation-in-part of Ser. No. 66,677, Jun. 26, 1987, Pat. No. 5,163,426, said Ser. No. 365,949, is a continuation-in-part of Ser. No. 66,677.

[51] Int. Cl.$^6$ .................................................. A61N 5/00
[52] U.S. Cl. ................................................ 607/88; 600/27
[58] Field of Search .................. 607/88, 90; 600/26–27; 315/158

[56] References Cited

U.S. PATENT DOCUMENTS

| | | |
|---|---|---|
| 1,187,672 | 6/1916 | Stiefvater . |
| 1,195,925 | 8/1916 | Hirsch . |
| 1,333,830 | 3/1920 | Burton . |
| 1,572,210 | 2/1926 | Kolibas . |
| 1,755,418 | 4/1930 | Anderson . |
| 2,268,156 | 12/1941 | Maddox . |
| 3,648,706 | 3/1972 | Holzer . |
| 3,773,049 | 11/1973 | Rabichev et al. . |
| 3,947,676 | 3/1976 | Battilana et al. . |
| 4,298,913 | 11/1981 | Lozar . |
| 4,463,284 | 7/1984 | Tamura et al. ................ 315/158 |
| 4,631,644 | 12/1986 | Dannhauer . |
| 4,734,834 | 3/1988 | Petzl et al. . |
| 4,794,496 | 12/1988 | Lanes et al. . |
| 4,858,609 | 8/1989 | Cole . |
| 4,901,211 | 2/1990 | Shen . |
| 4,911,166 | 3/1990 | Leighton et al. . |
| 5,006,985 | 4/1991 | Ehret et al. . |
| 5,079,682 | 1/1992 | Roberts . |
| 5,115,382 | 5/1992 | Smith . |
| 5,293,345 | 3/1994 | Gerardo . |

FOREIGN PATENT DOCUMENTS

| | | |
|---|---|---|
| 664887 | 9/1929 | France . |
| 747104 | 6/1933 | France . |
| 761765 | 3/1934 | France . |
| 2538503 | 6/1984 | France . |
| 3116958 | 12/1982 | Germany ............................ 607/88 |
| 333470 | 8/1930 | United Kingdom . |
| WO89/03235 | 4/1989 | WIPO ................................. 607/88 |
| WO89/08475 | 9/1989 | WIPO . |
| WO89/08476 | 9/1989 | WIPO ................................. 607/88 |

OTHER PUBLICATIONS

"Light Glasses", Moodlighters, Inc. (Jackson, MS)
"The Light Hat", The Light Hat (Jackson, MS).
"Light Glasses, A New Direction for Phototherapy", Moodlighters, Inc. (Jackson, MS).
Products & Services Brochure for Managers of Round-the-Clock Operations, Circadian Technologies, Inc. (1991 Ed.)
"Bio-Brite Light Visor™", *A New Way to Brighten Winter Days*, Instruction Manual, Bio-Brite, Inc. (1992).
"Healthy food, exercise can help beat jet lag", USA Today, Jan. 26, 1993.

*Primary Examiner*—Angela D. Sykes
*Attorney, Agent, or Firm*—Sterne, Kessler, Goldstein & Fox

[57] ABSTRACT

The present invention is an apparatus for producing and delivering high-intensity light to the eyes of a subject to modify the subject's circadian phase. The apparatus includes a support for positioning the apparatus above the eyes of the subject, a light generator for producing a cool, high-intensity light which is radiated to the eyes of the subject, and a power source coupled to the apparatus for supplying power to the light generator. The support of the invention is preferably a visor which does not obstruct the subject's vision when positioned on the head.

18 Claims, 6 Drawing Sheets

APPARATUS FOR PRODUCING AND DELIVERING HIGH-INTENSITY LIGHT TO A SUBJECT

RELATED U.S. PATENT APPLICATION INFORMATION

This application is a continuation-in-part of Ser. No. 07/882,172, filed May 8, 1992 now U.S. Pat. No. 5,304,212, now abandoned, which is a continuation-in-part of Ser. No. 07/819,403, filed Jan. 10, 1992 now U.S. Pat. No. 5,304,212, which is a continuation of serial number 07/365,949, filed Jun. 15, 1989 now U.S. Pat. No. 5,176,133, Ser. No 07/521,041 filed May 9, 1990, now U.S. Pat. No. 5,167,228, both of which are continuation-in-part of Ser. No. 07/066,677, filed Jun. 26, 1987, now U.S. Pat. No. 5,163,426.

FIELD OF THE INVENTION

The present invention relates to an apparatus for producing and delivering high-intensity light to the eyes of a subject to modify the subject's circadian phase. The apparatus may also be used to treat subjects suffering from jet lag, seasonal affective disorder and other conditions which may be affected by exposure to light.

BACKGROUND OF THE INVENTION

Scientific research has shown that the human body functions to the pace of an internal biological "clock". This clock, or circadian pacemaker as it is known in the art, is located in the brain and is regulated by exposure to natural or artificial light.

It has been found that humans tend to exhibit different degrees of alertness at different phases in their circadian cycle. Often, the activities in which humans wish to engage do not coincide with the most appropriate points in their cycle. Recent research indicates, however, that a subject's circadian cycle may be adjusted or shifted to better correlate the cycle with the subject's desired lifestyle.

Because the circadian cycle is regulated by light, exposure to carefully timed, high-intensity light is effective in adjusting the circadian phase by altering body temperature and secretion of the light-sensitive hormone melatonin. Additionally, exposure to high-intensity light has been found useful in treating certain psychiatric disorders (such as seasonal affective disorder and depression), jet lag, and chronic fatigue associated with "shift work" or the like.

U.S. Pat. No. 5,163,426 issued Nov. 17, 1992 to Czeisler et al. (Ser. No. 07/066,677, filed Jun. 26, 1987) discloses a lighting system for adjusting the circadian cycle. The system disclosed in this patent consists of large banks of fluorescent tubes or incandescent bulbs assembled within light "boxes" or "screens", or on adjustable stands, or illuminated goggles having small internal lamps. Although this system is capable of effectively adjusting the circadian cycle, it requires a large amount of energy, produces a significant amount of heat, and is not necessarily transportable.

In an effort to overcome the transportability and heat problems, light masks and other types of portable light systems to be worn on the head have been developed. One such example is disclosed in U.S. Pat. No. 4,858,609 to Cole. The Cole patent discloses a bright light mask having a reflective filter which minimizes heat delivery from the light to the user. The mask of the Cole patent, however, completely covers the eyes and does not allow the user to see. Obviously, this is not acceptable for individuals whose optimum treatment time is during the day when they must engage in other sight-requiring activities. Moreover, the mask of the Cole patent utilizes an incandescent bulb or green light emitting diode which produces a relatively low lux of light. Accordingly, the mask must be worn for long periods of time in order for the light treatment to be effective. This long treatment period may also be inconvenient for those whose optimum treatment time is during the day.

U.S. Pat. No. 4,911,166 to Leighton et al. discloses delivering light from an incandescent bulb to a patient's eyes for treatment of seasonal affective disorder. The bulb of the device is affixed to a transportable, adjustable structure which is worn on the user's head. Although the device of the Leighton patent does not cover the user's eyes, it obscures the user's vision. Specifically, the incandescent bulb of the device is positioned immediately in front of the user's eyes thereby physically blocking the user's field of vision. Moreover, light radiated from the bulb is focused into a cone by a fresnel lens which then projects the light directly into the user's eyes. Because the light is projected into the eye in such a manner, the user's field of vision is obscured thereby inhibiting the user's activity, as he is incapable of seeing beyond or around the light. Further, the device of the Leighton patent generates a high amount of heat because it utilizes an incandescent bulb. Further, the lens of the device must be specifically positioned in relation to the eye in order for the treatment to be effective.

Some light delivery systems do allow the user to see when the device is in use. For example, the LIGHT VISOR™ by Bio-Brite, Inc. employs a visor worn above the eyes which does not obscure the user's field of vision. The Bio-Brite device, however, utilizes an incandescent bulb which is not capable of generating high-intensity light (i.e. light measuring greater than 4,000 lux). Thus, treatment periods via the Bio-Brite device may be unnecessarily lengthy. Further, because the light of the device is adjustable, the photometrics are imperfect for modification of the circadian phase, as light generated by the device may be improperly projected to the eyes of the user. Finally, the light generated by the Bio-Brite device is columnated (that is, the photons of light travel in parallel columns) which can be uncomfortable to the user's eyes.

Still other devices (such as those disclosed in U.S. Pat. Nos. 1,187,672, 4,794,496 and 4,911,166) are heavy and uncomfortable, or are awkward in shape and therefore interfere with the user's head and body movements.

It was with these problems in mind that the present invention was developed. Accordingly, a primary objective of the present invention is to provide a lightweight and portable light source capable of generating a high-intensity light which will accomplish modification of the human circadian cycle.

Another objective of the present invention is to provide a light source and delivery system which simulates naturally occurring overhead light entering a person's eyes.

Another objective of the invention is to provide a high-intensity light which does not produce and radiate a high amount of heat to the eyes of the user.

Still another objective is to provide a light producing and delivery system which reliably delivers light to the eyes of the user regardless of the position of the user's head.

Another objective of the present invention is to provide a light producing and delivery system which affords the user maximum visibility by occupying a relatively small portion of the user's peripheral field of vision when the system is in use.

Yet another objective of the invention is to provide a light system which does not consume a large amount of energy.

SUMMARY OF THE INVENTION

To achieve the foregoing and other objectives, an apparatus for producing and delivering light to the eyes of a subject for treatment of physiologic and psychiatric disorders affected by exposure to light is provided. The apparatus includes a bodily-worn support means for removably positioning the apparatus vertically above the eyes of the subject, at least one light generating means supported by the support means, and a power source coupled to the light generating means to supply power to the light generating means. The support means affords the subject an unobstructed field of vision when the support means is positioned above the eyes. The light generating means produces a cool, high-intensity light which is radiated to the eyes of the subject.

The support means may take the form of a visor, while the light generating means may be a cold cathode lamp capable of generating a light of at least 10,000 lux. The light generating means may be positioned on the bill of the visor to deliver light to the eyes. The power source may be a direct current source or an alternating current source. An invertor for converting low voltage direct current to high-frequency, high-voltage alternating current is also provided.

The visor may be provided with an adjusting means and a cushioning means for imparting a comfortable, secure fit to the user. The apparatus may be further provided with a shield disposed between the light generating means and the eyes of the subject for faltering out harmful radiation while transmitting substantially all visible light. A reflector may also be provided for projecting toward the subject all back-reflected light generated by the light generating means. A control means for regulating the timing and intensity of a light treatment schedule may also be incorporated into the apparatus via a conventional connecting means.

In another aspect, the present invention is an apparatus for projecting light to the eyes of a subject. The apparatus includes a support structure positioned proximate the head, a light source of the cold-cathode lamp type, and a power source for providing power to the light source. The support structure includes a visor having a bill portion which extends vertically above the eyes and a headband portion which is adapted to be positioned about the head of the subject. The light source is mounted under the bill of the visor to radiate light of high-intensity and low temperature to the eyes of the subject. A coupling means connects the power source to the light source.

The support structure of this aspect of the invention may also include a shield for filtering out harmful radiation and transmitting substantially all visible light. A reflector may also be provided for projecting toward the subject back-reflected light produced by the light source. Finally, a controlling means which controls the timing and intensity of a light treatment schedule derived from a prescribing means may be connected to the apparatus via a conventional connecting means.

BRIEF DESCRIPTION OF THE DRAWINGS

Various objects, features, and attendant advantages of the present invention will be more fully appreciated as the same becomes better understood from the following detailed description of the present invention when considered in connection with the accompanying drawings in which.

DESCRIPTION OF THE PREFERRED EMBODIMENT

Referring now to the drawings, wherein like reference numerals represent identical or corresponding structure throughout the figures of the application, the apparatus of the present invention is illustrated generally at 10 in FIGS. 1–4. The apparatus essentially comprises a support or housing 12, a light generating means 14 (see FIG. 3), and a power source 16. Support 12 takes the form of a conventional visor having a bill 18 and a headband 20. The visor is preferably molded from a thermoplastic material such as polycarbonate commercially available under the trademark LEXAN. However, it should be realized by those skilled in the art that the support may be formed from any heat stable, lightweight, rigid and durable material which allows the component parts of the apparatus to be securingly affixed thereto.

In the preferred embodiment, bill 18 is generally crescent-shaped and comprised of an upper surface 22, a lower surface 24, a proximal end 26 and a distal end 28. Bill 18 is approximately 17 mm thick at proximal end 26 and tapers to a thickness of approximately 10 mm at distal point 30. From central axis X, bill 18 extends at an angle θ of approximately 20°.

Figure 1:
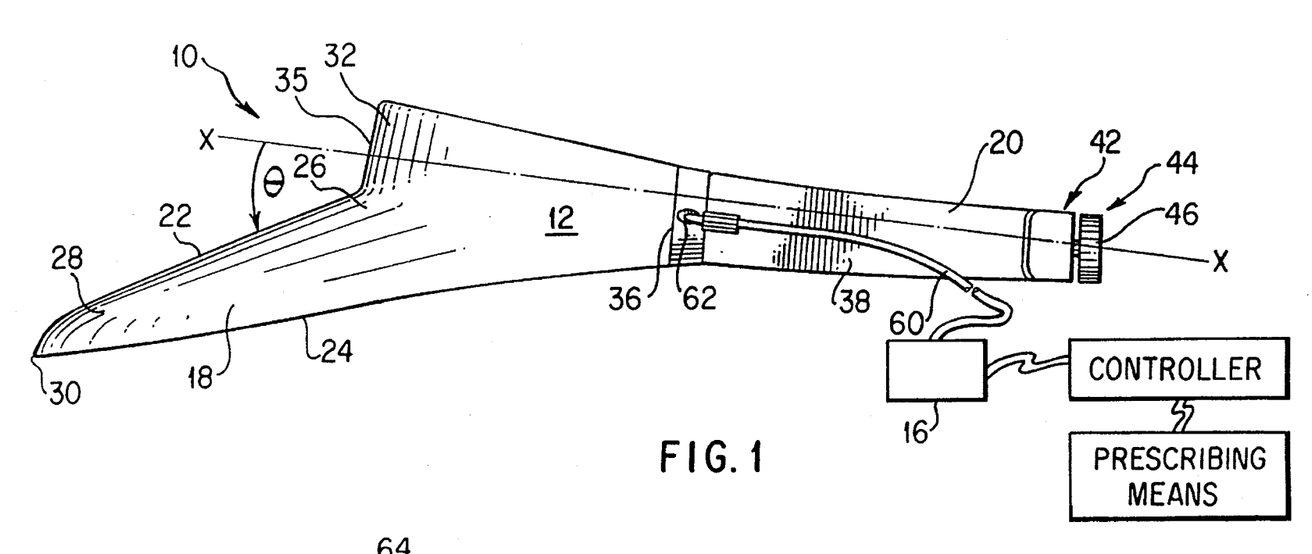
FIG. 1 is a side elevational view of the light producing apparatus of the present invention.
Figure 2:
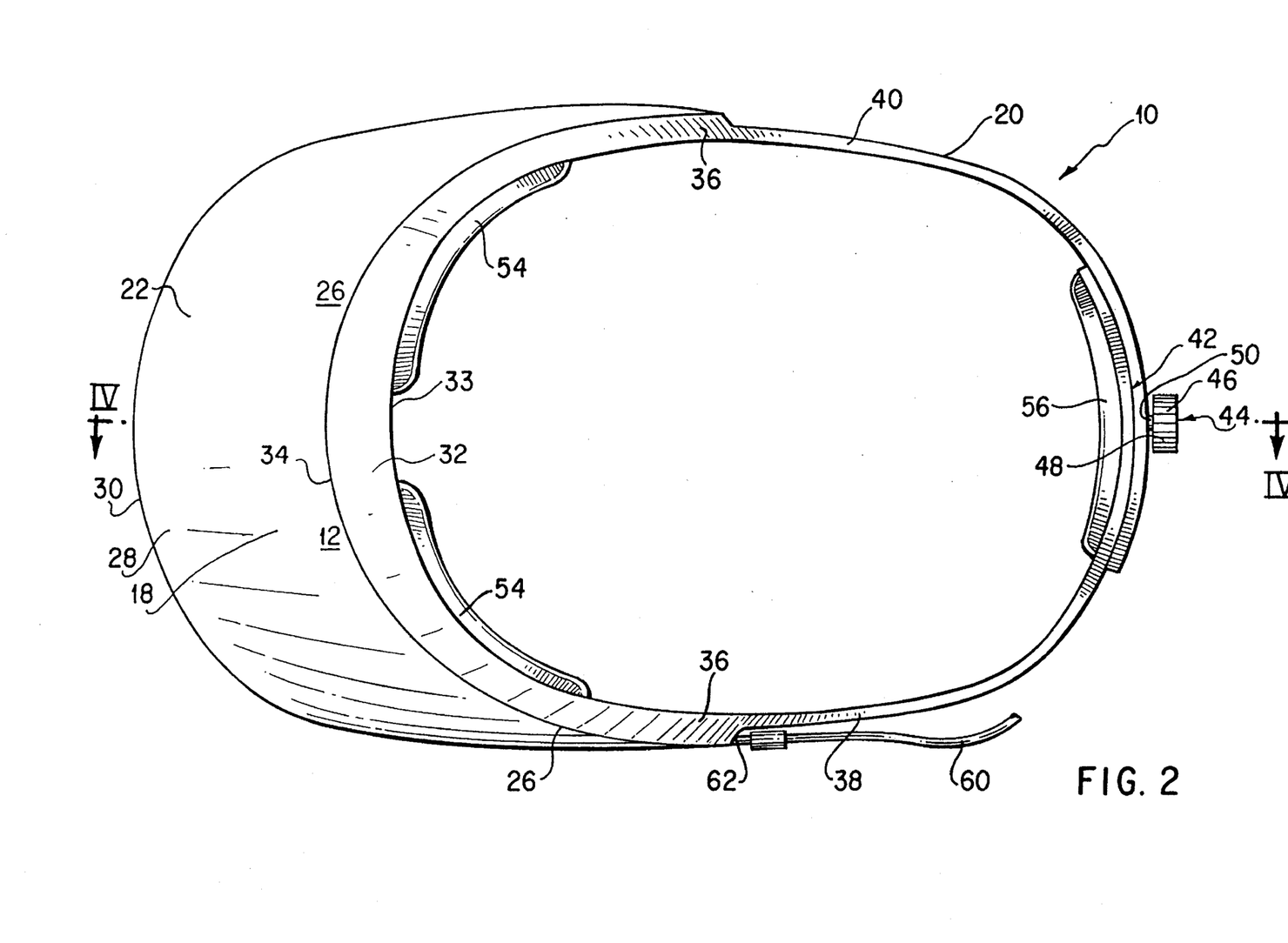
FIG. 2 is a top plan view thereof.
Figure 3:
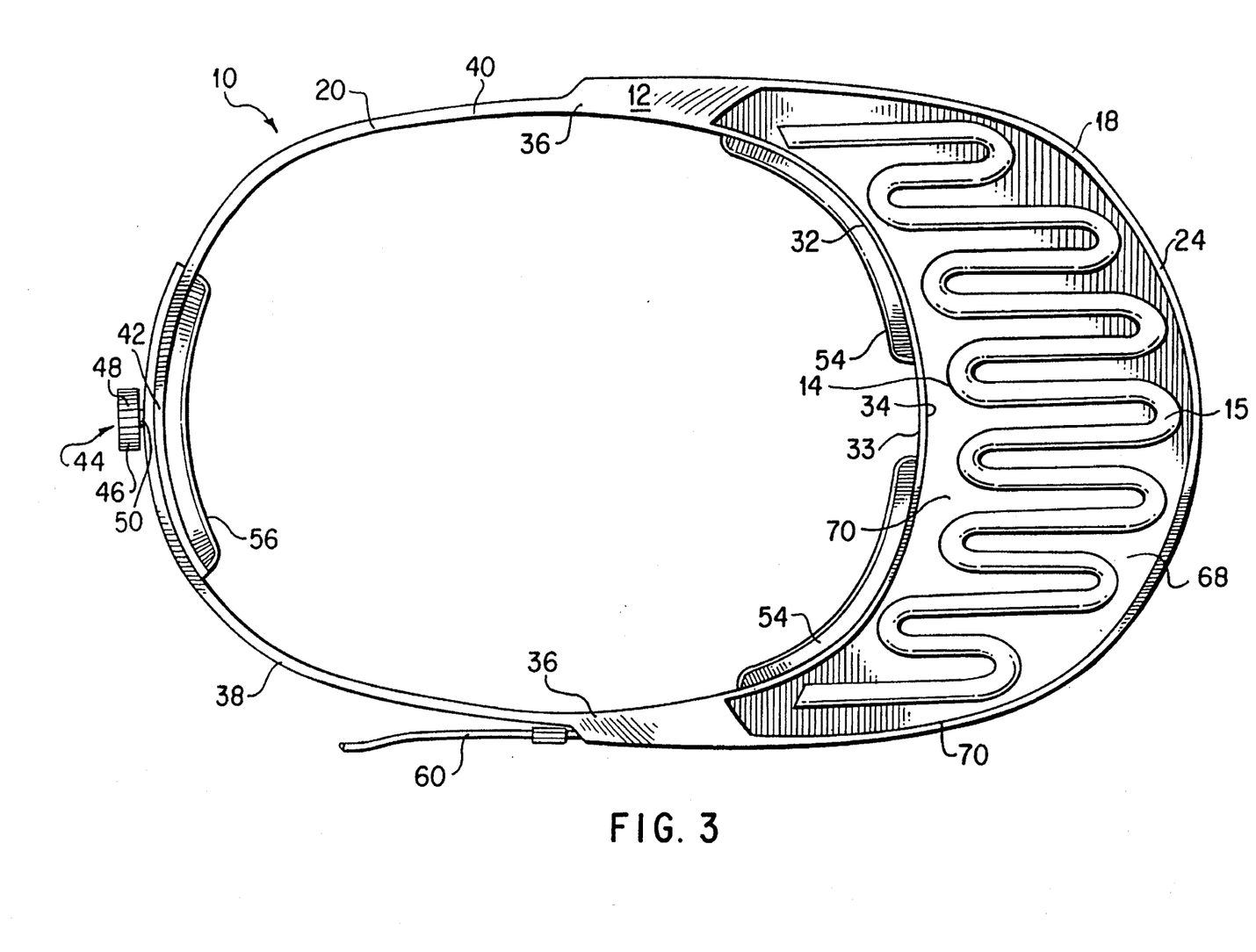
FIG. 3 is a bottom plan view thereof.
Figure 4:
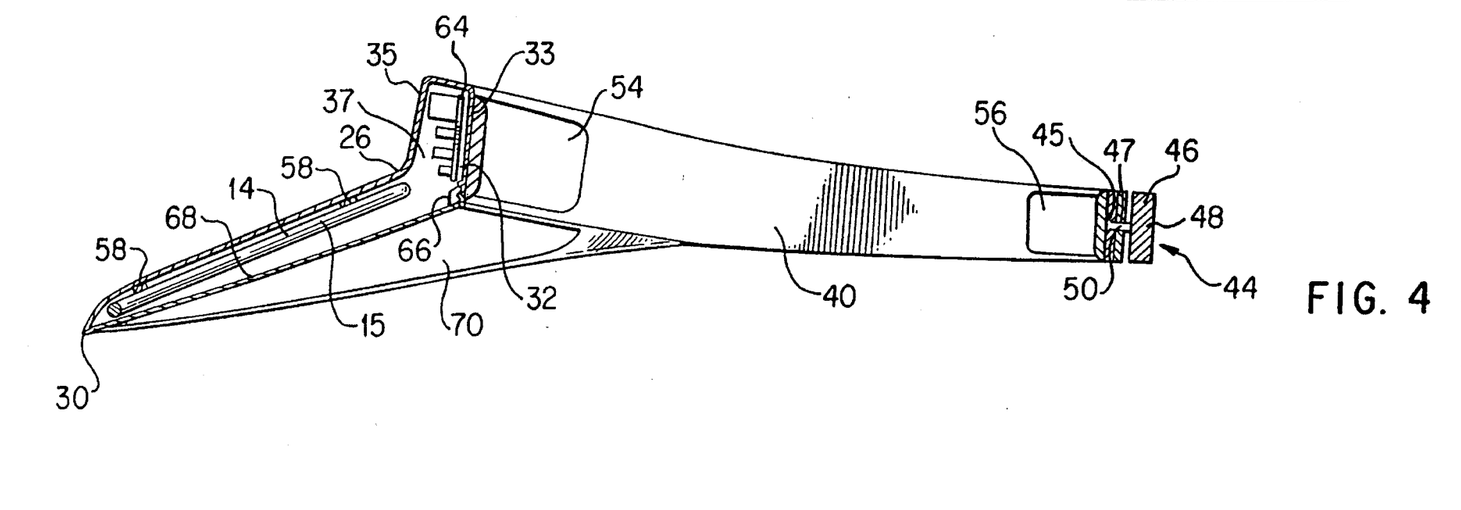
FIG. 4 is a cross-sectional view thereof taken along line IV—IV of FIG. 2.
Figure 5:
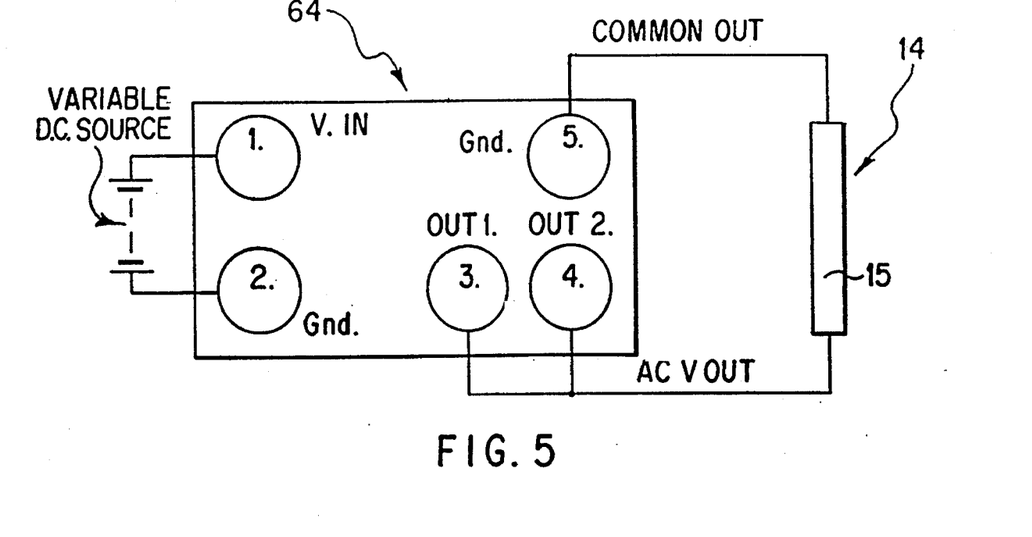
FIG. 5 is a circuit diagram of the power invertor.

At proximal end 26, bill 18 extends upwardly (approximately 37.5 mm) into a u-shape to form a forehead engaging surface 32 (see FIG. 4). Forehead engaging surface 32 extends around inner periphery 34 of bill 18 to follow the profile of the human forehead. Forehead engaging surface 32 includes an inner surface 33 and an outer surface 35 which define therebetween an interior area 37. At ends 36, forehead engaging surface 32 merges with headband 20 of support 14. Headband 20 is generally circular in plan and is comprised of a right or first extension 38 and a left or second extension 40. Extensions 38 and 40 overlap each other at the rear of the headband and are fastened together at 42 to secure the headband of the visor to the head of the user. Extensions 38 and 40 are approximately 35 mm in width and adjustably overlap each other to comprise the circumferential dimensions of the head. Extensions 38 and 40 should be flexible enough to conform to the shape of the user's head, yet rigid enough to support the bill of the visor. Alternatively, headband 20 may consist of left and right ear pieces such as those illustrated in FIGS. 6 and 9. This alternative configuration, however, is not as supportive as that illustrated in FIGS. 1–4 because the ear pieces do not completely encircle the user's head.

Left and right extensions 38 and 40 may be fastened together using any conventional fastening means capable of adjustably securing the extensions together. Fastening means 44 shown in the figures includes a polymeric thumb screw 46 having a head 48 and a threaded stem 50 which extends through extensions 38 and 40 (see FIG. 4). Screw 46 is inserted into hole 45 and slot 47 provided in extensions 38 and 40, respectively to fasten extensions 38 and 40 together. When the user wishes to adjust headband 20, screw 46 is unscrewed, extensions 38 and 40 are repositioned relative to each other, hole 45 and slot 47 are re-aligned as desired, and screw 46 is tightened to securingly fasten the extensions together.

Cushioning for headband 20 is provided to the user by cushions 54 affixed to inner surface 33 of forehead engaging surface 32. Cushions 54 distribute contact pressures over large areas of the forehead to impart instant and long term comfort thereto. Cushions 54 also assist in providing a secure fit between inner surface 33 of visor 12 and the user's head. Pads 54 are preferably formed from any low durometer closed-cell elastomeric foam which has been approved for topical use by the Food and Drug Administration. Other cushioning materials which are non-toxic and non-allergenic may be also used to form cushions 54. Although two separate cushion pads 54 are illustrated, those skilled in the art should realize that a single elongated pad may also be utilized. If desired, cushion pad 56 may also be provided on the inner surface of headband extensions 38 or 40 to cushion the back of the user's head.

Turning now to FIGS. 3 and 4, light generating means 14 of the present invention is shown. Specifically, a cold-cathode fluorescent lamp 15 for generating light is fixedly mounted to lower surface 24 of bill 18 by a non-adjustable mounting means 58. A non-adjustable construction ensures that light of a high-intensity is always properly projected to the eyes of the user for effective adjustment of the circadian phase. Thus, the user need never be concerned with the directionality of the light and is therefore free to engage in other activities while wearing the visor. Mounting means 58 is an elastomeric adhesive which is capable of absorbing impact to housing 12. Mounting means 58 is preferably formed from a temperature stable, silicone elastomer having a Shore A durometer hardness of 20–30. Mounting means 58 may be formed from any other elastomeric adhesive having the aforedescribed hardness and temperature tolerating characteristics. As illustrated in FIG. 4, two mounting means 58 are provided by placing a dollop of adhesive on bill 18 to securingly affix light generating means 14 thereto. The dollops level off to an area approximately 5 mm long, 5 mm wide, and 2 mm thick. Mounting means 58 are spacingly positioned from each other on the lower surface of bill 18 at a distance of approximately 45 min. It should be apparent to those skilled in the art that the number of mounting means may be varied depending upon the size and weight of light generating means 14 and the dimensions of bill 18. Light generating means 14 is specifically positioned on bill 18 at a distance D (FIG. 6) which is approximately 22 mm above the eyes (measured vertically from the surface of light generating means 14 to the pupil of the user's eye) so that light is radiated to the eyes from within the extreme peripheral field of vision. Positioning of light generating means 14 in such a manner produces a light which appears more natural to the user, a primary objective of the present invention. Moreover, radiation of light from within the extreme peripheral field of vision allows the user to move his head without affecting the amount of light delivered to the eyes. The significance of the peripheral field of vision will be discussed below in greater detail.

Light generating means 14 of the present invention is unlike those of prior devices in that it is capable of producing a naturally colored, high-intensity, cool light. Cold-cathode lamp 15 is preferably formed as a 5 mm diameter, 1 mm thick circular glass tube. Prior to forming the glass tube, the interior surface thereof is lined with a phosphor compound which is cured thereto by application of heat. The phosphor compound of the present invention is preferably 5000° Kelvin temperature grade phosphor having spectral properties which simulate naturally occurring light (that is, the spectral distribution of the described phosphor is balanced). Each end of lamp 15 is enclosed by application of heat, thereby liquefying the glass to form a pressure tight seal. Within each pressure tight seal, an electrode encapsulated within a pressurized gas is provided.

In one aspect of the invention, the electrodes consist of an electrical lead used in conjunction with an unsecured amount of mercury encapsulated within the end of the lamp. The mercury is of the standard triple distilled type which is a free flowing liquid in use. In another aspect, the electrodes are comprised of a titanium mercury alloy which form an intermetallic compound $Ti_3Hg$. Following insertion of the electrodes into the tube, the alloy is heated (by infra-red radiation, laser beam, induction heating or other suitable means) over 500° C. for a temporary period under a vacuum or in an inert atmosphere where the titanium mercury lattice then becomes unstable or activated. Activation of the lattice during fabrication of the tube results in the lattice releasing approximately 70% of the total mercury content. The balance of the mercury is released into the pressurized gas tube during normal operational heating of the device. The pressurized gas within the tube is preferably commercially available argon gas having a purity of approximately 99.998%. The argon gas is dispensed into the tube (at approximately 13 mm of pressure to adequately pressurize the tube) during sealing of the electrodes within the tube. Complete excitation of the phosphor lining within the tube is critical in order to achieve emission of a light suitable for adjustment of the circadian phase. The specific gas and electrode composition encapsulated within the tube of the present invention is capable of exciting the phosphor lining to the appropriate level upon introduction of a high-voltage, high-frequency current which will be discussed in greater detail below. The light emitted by the phosphor lining is not only of high intensity but also possesses a coloring index which closely simulates naturally occurring light. Thus, the emitted light is comfortable to the user and does not unnaturally discolor the user's immediate environment, an objective of the present invention.

Lamp 15 functions at a low temperature to produce a light of at least six steridians and up to 25,000 lux or 4.5 lamberts. The operating temperature of lamp 15 ranges from approximately 32° to 66° C. Another advantage of the fluorescent lamp is that it is very energy efficient. For example, lamp 15 can produce 85–90 lumens of light per watt compared to 25–30 lumens of light per watt produced by standard incandescent light bulbs. Thus, the light produced and radiated by lamp 15 is highly luminous, comfortable to the user and energy efficient. Lamp 15 is compact in nature, as it is mounted onto bill 18 of the visor in a serpentine configuration. The tube is configured in a serpentine fashion to maximally cover the undersurface of the bill in order to meet the required illuminance level for that surface (i.e. light of a circadian adjusting level). Preferably, lamp 15 is originally 650 mm in length and bent 14 times to yield a tube approximately 225 mm in consolidated length. Further, the serpentine configuration allows light produced by the entire length of the tube to be projected to the user from within the extreme peripheral field. Of course, other configurations which render the lamp compact are also suitable. A cold-cathode lamp producing a lower intensity of light may also be utilized for general tasks such as reading, sewing, etc. A dimmer switch may also be provided on the apparatus to gradually increase or decrease the intensity of lamp 15.

Power is supplied to light generating means 14 by a power source 16 through a power invertor 64. The current generated by the power source may be direct or alternating. If the power source supplies alternating current, the current is first converted to a low voltage direct current and then converted to a high voltage alternating current by power invertor 64. In one aspect of the invention, apparatus 10 is rendered transportable via a remote compact battery pack which may be positioned on the user's body (for example, clipped onto a belt). The battery pack provides up to 10 watts of power to energize apparatus 10 through invertor 64. Batteries having an output of 5 volts and a discharge rate of 1.6 amps provide sufficient power to energize light generating means 14. The battery pack may be coupled to the apparatus of the present invention by a d.c. input jack cord 60. The d.c. input jack cord is of the insulated 22 AWG type. Cord 60 is inserted into a conventional d.c. input jack 62 provided within the visor near ends 36 of the forehead engaging surface. The jack is inserted into the apparatus to supply the required direct current to the apparatus and may be conveniently removed when the battery pack is not in use.

The d.c. input jack is electrically connected to a power invertor 64 disposed within interior area 32 of visor 14. Invertor 64 is preferably placed in close proximity to lamp 15 within housing 12 to decrease resistance and assure delivery of adequate power to lamp 15. Placement of invertor 64 within housing 12 also protects the user against potential shocks. Invertor 64 is provided to convert the relatively low d.c. input voltage from the battery into a relatively high a.c. output voltage at relatively high frequencies. The input voltage required by the invertor is designed to be low such that batteries can be used in series with minimal residual energy left over. This design assures a minimal interval in which the batteries are providing less than the rated voltage. By properly designing a match between lamp 15 and invertor 64, unwanted over current and under current conditions can be eliminated. For example, an over current condition will create excess heat through the glass tube which will in turn be radiated to the user. On the other hand, an under current condition can produce deviant electrical waveforms which interfere with nearby electrical devices. In keeping with this objective, the electrical output of invertor 64 is a high frequency current drawing approximately 0.5–1.5 amps at 5 volts (direct current) and generating output (alternating current) between 600–900 volts at frequencies between 25,000 and 30,000 kHz. An output of such a voltage and frequency properly excites the pressurized argon and mercury vapor within the glass tube to achieve emission of light from the phosphor appropriate for adjustment of the circadian phase. Preferably, a sinusoidal waveform is employed, as such a waveform is better suited for excitation of the gas molecules. The power invertor is electrically connected to the light generating means 14 by standard electrical contacts (not shown) to supply the alternating current thereto. Alternatively, if the user intends on remaining stationary during the treatment period, the d.c. input jack will also accept an a.c.-to-d.c. wall adaptor. A circuit breaker 66 is further provided to cut off all electrical output to the light generating means to enable the user to safely replace the cold-cathode lamp when needed. The circuit breaker is a single pole, normally off mechanical microswitch.

Provided between light generating means 14 and the user is a shield 68. Shield 68 extends from proximal end 26 to distal end 28 of bill 18 to completely cover light generating means 14. It is securingly mounted to bill 18 by a mechanical hinge to allow replacement of lamp 15 when needed. Shield 68 is provided to protect cold-cathode lamp 15 from impact or contact with objects. Shield 68 is capable of filtering out harmful ultra violet radiation while transmitting virtually all visible light. The shield is preferably formed from a transparent polycarbonate; however, any other temperature stable material which is capable of filtering out harmful radiation and transmitting visible light may also be utilized.

Finally, a diffuse reflector 70 is coated on lower surface 24 of bill 18 (see FIG. 3). Reflector 70 forwardly projects diffuse back-reflected light from lamp 15. The reflective material utilized on lower surface 24 may be composed of either magnesium oxide or titanium dioxide with an organic binder. Other suitable heat stable, reflective materials may be utilized to forwardly project back-reflected light.

Having described the component parts of the present invention, its use will now be described. After assessing the circadian cycle of the subject, modification of the cycle is formulated using theoretical and empirical foundations. Such assessment and modification techniques are disclosed beginning, for example, at column 10, line 12 of U.S. Pat. No. 5,163,426 issued Nov. 17, 1992 to Czeisler et al. (pages 21–50 of U.S. application Ser. No. 07/066,677, filed Jun. 26, 1987), the complete disclosure of which is hereby incorporated by reference. Computer hardware and software capable of prescribing the timing and intensity of an individual user's phototherapy regimen is also disclosed. For example, the software program accepts a library of information about the user's current circadian cycle and activity characteristics. The program then automatically calculates ant optimal lighting regimen and sends it to a remotely located controller which may be coupled to the apparatus via a conventional electrical connector to automatically control the timing and intensity of the light. The regimen may be adjusted by the controller as needed depending upon the user's activity (e.g. cross-meridian air travel). The controller may also include a clock and timer which automatically starts and stops the phototherapy session in accordance with various timer settings. Further, the controller may be provided with a manual override switch which allows the user to manually initiate (or interrupt) the phototherapy regimen based upon information provided by the controller to the user. The controller may also provide a dimming function whereby the intensity of lamp 15 is gradually increased or decreased at the beginning and end of a treatment cycle, affording the eyes time to adjust to the high-intensity light. A manual dimmer switch may also be provided on the visor for the same purpose, or to simply decrease the intensity of light generated by lamp 15 if the visor is used for general lighting purposes.

When it is desired to apply light to the subject, the subject places visor 12 on his head. If visor 12 is not comfortably secured to the subject's head, headband 20 may be adjusted in a manner heretofore described. Power, from either the battery pack or an a.c. wall outlet, is supplied to power invertor 64 where it is converted into high-voltage alternating current and then transferred to light generating means 14 of the present invention. As previously described, light generating means 14 produces up to 4.5 lamberts of light measured at the surface of light generating means 14, by way of cold-cathode lamp 15. Lamp 15 provides up to 14,000 lux of light measured within six steridians at a distance equal to the distance between light generating means 14 and the eyes of the subject wearing apparatus 10. If a dimmer switch is provided, the light is gradually ramped to its maximum intensity affording the eyes time to adjust to the high-intensity light. When the phototherapy regimen is completed, the intensity of light is gradually ramped down by the dimmer switch giving the user's eyes time to adjust to ambient light. The generated light is radiated to the subject through filtering shield 68. Harmful ultra violet light from lamp 15 is blocked by the shield, while substantially all visible light is transmitted therethrough to the user. Back-reflected light from lamp 15 is diffusely reflected by reflector 70 and forwardly projected to the subject's eyes through shield 68. The light radiated to the subject may be of an intensity suitable for modification of the circadian phase and treatment of the other aforedescribed disorders. The light delivered to the subject is cool in temperature compared to incandescent light sources producing the same amount of light within equal proximity to the subject's eyes. Moreover, the radiated light is diffuse (as opposed to columnated) and distributed in an uniform manner so that it is comfortable to the user.

Figure 6:
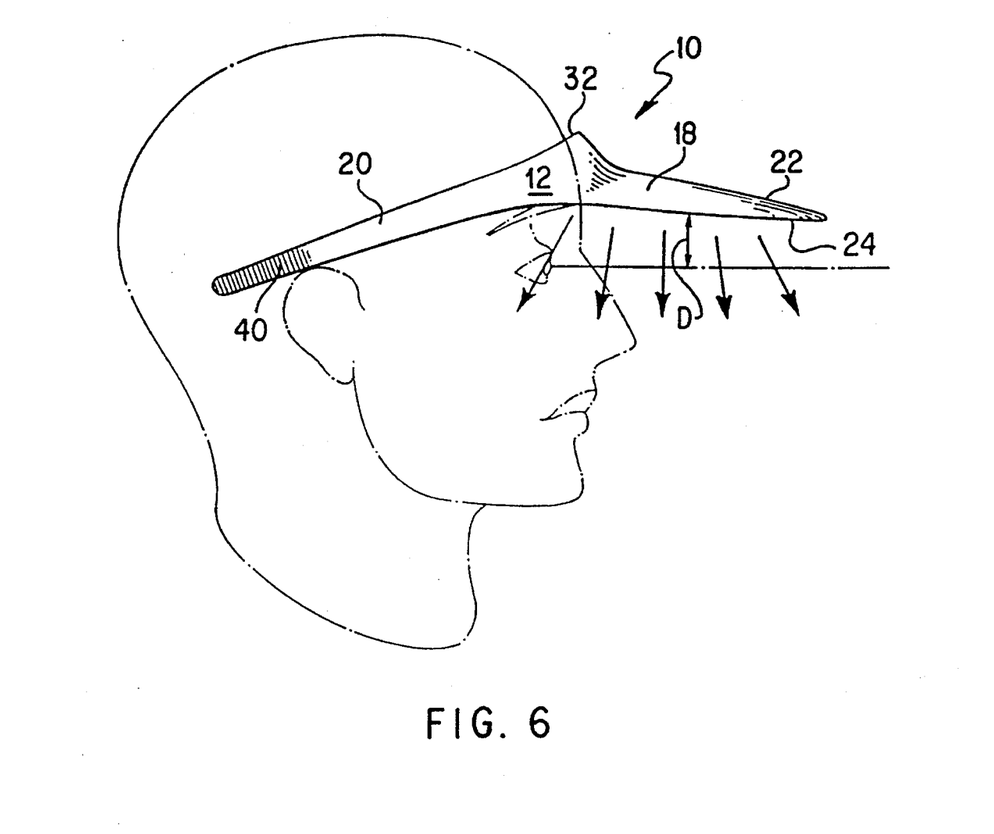
FIG. 6 is a side elevational view of the apparatus in use.
Figure 7:
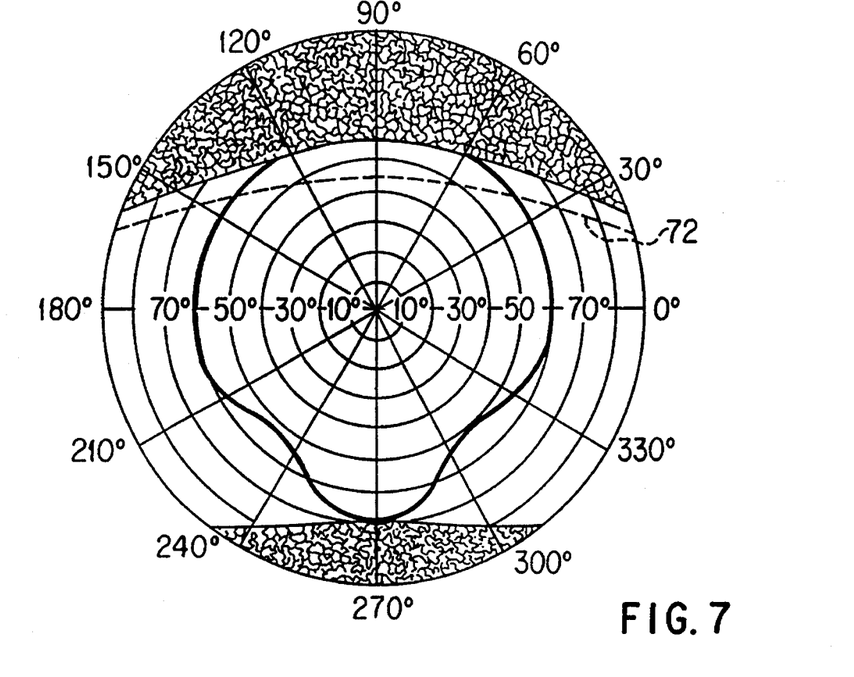
FIG. 7 illustrates the normal field of vision for a pair of human eyes and the field of vision cut off by the eyebrows, cheeks and nose.
Figure 8:
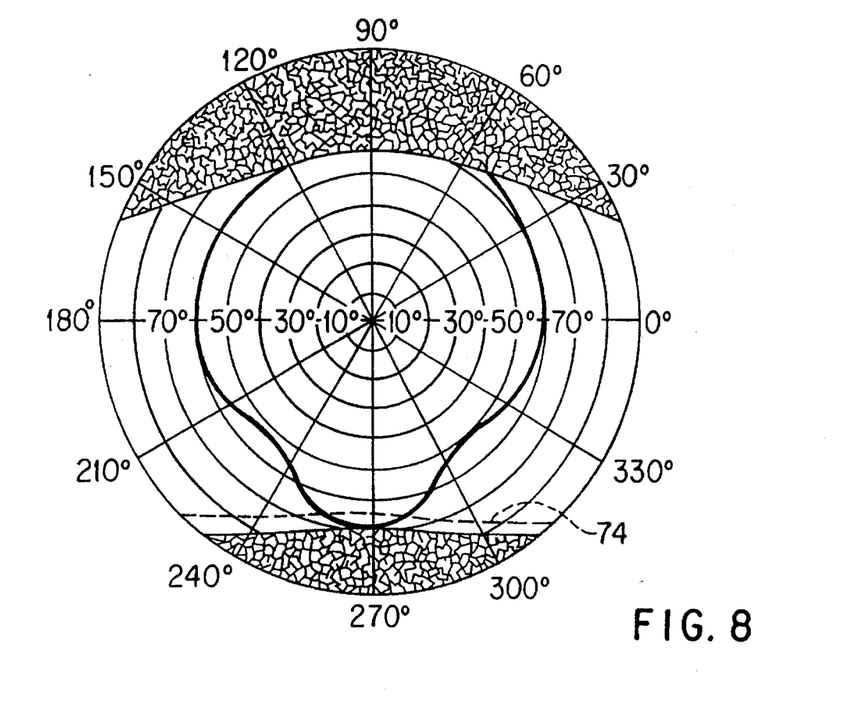
FIG. 8 illustrates the normal field of vision for a pair of human eyes and the field of vision cut off by reflection of light from the face.

During application of light therapy, the subject need not be concerned with the position of his head, as the non-adjustable placement of lamp 15 beneath bill 18 assures that the correct amount of light needed for effective therapy reaches the subject's eyes, as the light is radiated to the eyes from within the extremities of one's peripheral field of vision (see FIG. 6). Additionally, the visor of the present invention is superior to that of prior devices, as it does not appreciably obscure the subject's field of vision, allowing him to engage in sight-requiring activities simultaneously. By way of illustration, FIG. 7 depicts the normal field of vision for a pair of human eyes. The inner white portion of the field equals binocular vision, while the outer white portion equals the monocular left and right fields. The black portions at the top and bottom of the field represent the field of vision cutoff by the eyebrows, cheeks, and nose. Dotted line 72 represents the field of vision occupied by the apparatus of the present invention. As can be seen, the apparatus occupies a relatively small area of the subject's field of vision, thereby affording practically unobscured vision. The field of vision occupied by light reflected by the subject's nose and cheeks is represented by dotted line 74 in FIG. 8. Again, the reflected light of the present apparatus occupies a very small area of the subject's peripheral field of vision. Thus, the present invention achieves the objective of a light source analogous to regularly occurring indoor or outdoor light which does not obscure the subject's peripheral field of vision. Moreover, the light projected to the subject is quite comfortable, as it is diffused, of natural color and cool in temperature.

Figure 9:
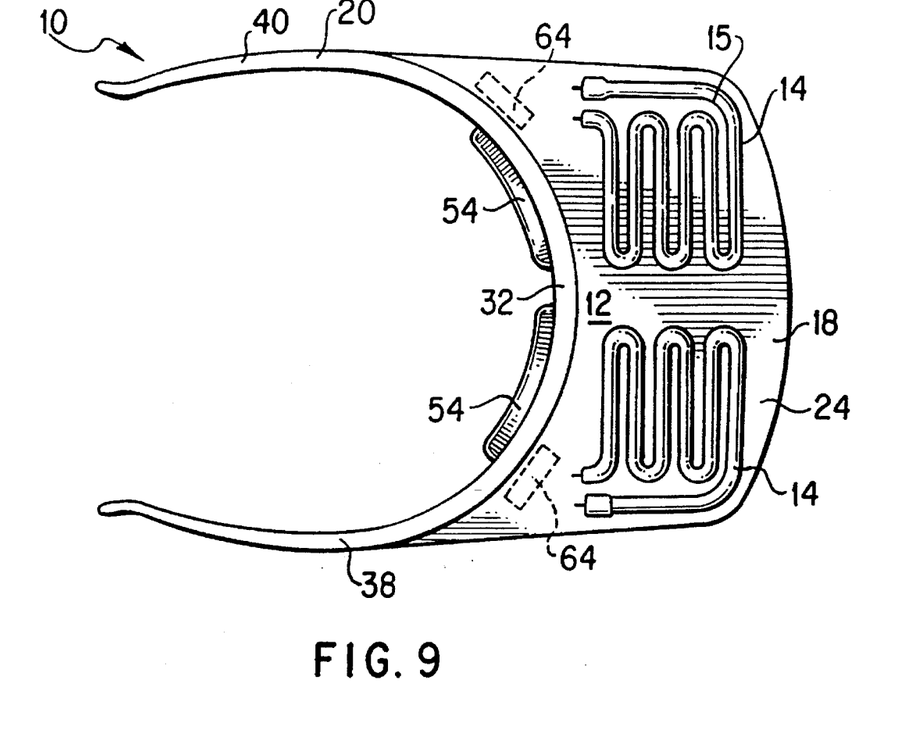
FIG. 9 is an alternate embodiment of the apparatus of the present invention.
Figure 10:
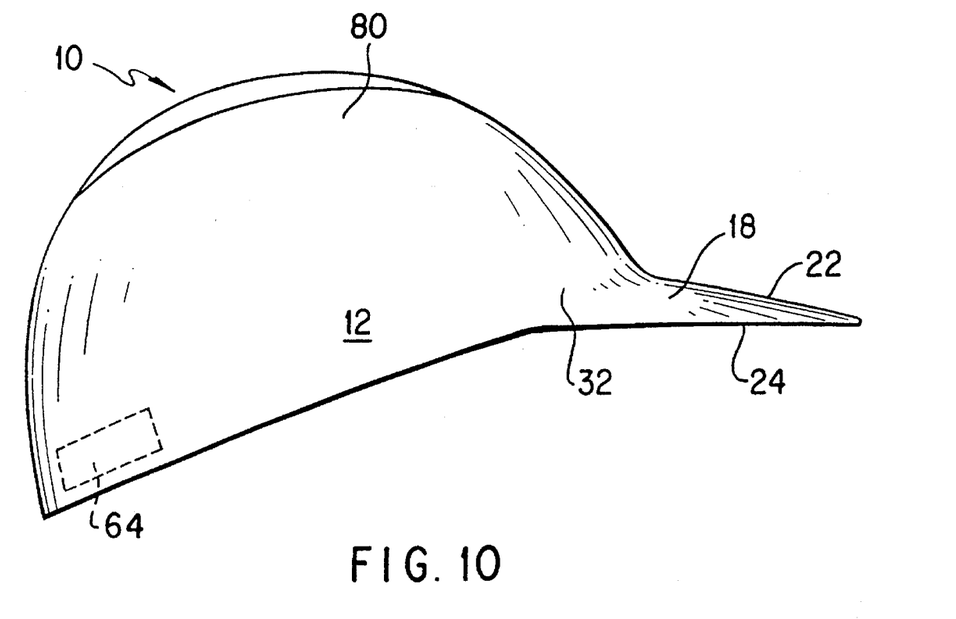
FIG. 10 is another alternate embodiment of the apparatus of the present invention.

It is to be understood by those skilled in the art that the foregoing is considered illustrative of the principles of the invention. The invention is not be limited to the details given herein, but may be modified within the scope of the following claims. For example, as illustrated in FIG. 9, the light generating means of the present invention may include two cold-cathode lamps 15 which, although not shown, are electrically connected to two separate power invertors 64. Moreover, the light producing and delivering apparatus of the invention need not be open at the crown as illustrated, but may instead be formed as a hat such as that shown in FIG. 10 which includes a crown 80 in addition to a bill 18 and headband 20.

We claim:

1. A bodily worn apparatus for producing and delivering light to the eyes of a subject for treatment of physiologic and psychiatric disorders affected by exposure to light, comprising:

support means for removably positioning said apparatus on the head of the subject vertically above the eyes of said subject, said support means affording the subject a generally unobstructed visual field when said support means is positioned on the head of the subject above the eyes;

at least one cool, high-intensity, light generating means including a cold cathode lamp supported by said support means for producing a cool, high-intensity light; and a power source coupled to said light generating means for supplying power to said light generating means.

wherein the temperature of said cool, high-intensity light produced and radiated to said subject by said light generating means is comfortable to said subject, allowing said subject to wear said apparatus for an extended period of time.

2. The apparatus of claim 1, wherein said support means is a visor having a bill and a headband.

3. The apparatus of claim 2, wherein said light generating means is non-adjustably mounted on said bill of said visor.

4. The apparatus of claim 2, further comprising a reflector to project out from the bill back-reflected light generated by said light generating means.

5. The apparatus of claim 1, wherein said power source is a direct current source.

6. The apparatus of claim 5, wherein said direct current source is a battery.

7. The apparatus of claim 5, further comprising an invertor for converting said direct current to a high-frequency, high-voltage, low ampere alternating current.

8. The apparatus of claim 1, wherein the operating temperature of said cold cathode lamp ranges from approximately 32° to 66° C.

9. The apparatus of claim 1, further comprising a means for adjusting said support means.

10. The apparatus of claim 1, further comprising a shield disposed between said light generating means and the eyes of said subject for filtering out harmful radiation while transmitting substantially all visible light.

11. The apparatus of claim 1, wherein said light generating means generates a light of approximately 10,000 lux.

12. The apparatus of claim 1, further comprising a means for prescribing the timing and intensity of a light treatment schedule using said apparatus.

13. The apparatus of claim 12, further comprising a controlling means which controls said apparatus based upon the treatment schedule derived by said prescribing means.

14. The apparatus of claim 13, further comprising a means for connecting said apparatus to said control means.

15. A bodily worn apparatus for projecting light to the eyes of a subject, comprising:

a visor having a bill which extends over the eyes of the subject and a headband which is adapted to be positioned about the head of the subject;

a cold-cathode fluorescent lamp mounted on said bill of said visor for producing light;

a power source disposed on said visor for supplying power to said lamp; and means for coupling said lamp to said power source;

wherein the temperature of the light produced and radiated to said subject by said cold-cathode fluorescent lamp is comfortable to said subject, allowing said subject to wear said apparatus for an extended period of time.

16. The apparatus of claim 15, further comprising a shield disposed between said lamp and said subject for filtering out harmful radiation while transmitting substantially all visible light.

17. The apparatus of claim 15, wherein the operating temperature of said cold cathode lamp ranges from approximately 32° to 66° C.

18. The apparatus of claim 15, further comprising a reflector to project toward the subject back-reflected light produced by said lamp.

* * * * *